(12) United States Patent
Grassauer et al.

(10) Patent No.: US 8,282,969 B2
(45) Date of Patent: Oct. 9, 2012

(54) ANTIVIRAL COMPOSITION AND METHOD OF USE

(75) Inventors: Andreas Grassauer, Vienna (AT); Eva Prieschl-Grassauer, Vienna (AT); Christiane Koller, Seyring (AT); Alexander Pretsch, Roseldorf (AT)

(73) Assignee: Marinomed Biotechnologie GmbH, Vienna (AT)

( * ) Notice: Subject to any disclaimer, the term of this patent is extended or adjusted under 35 U.S.C. 154(b) by 244 days.

(21) Appl. No.: 12/312,926

(22) PCT Filed: Dec. 4, 2007

(86) PCT No.: PCT/EP2007/010512
§ 371 (c)(1),
(2), (4) Date: Aug. 3, 2009

(87) PCT Pub. No.: WO2008/067982
PCT Pub. Date: Jun. 12, 2008

(65) Prior Publication Data
US 2010/0040658 A1    Feb. 18, 2010

(30) Foreign Application Priority Data
Dec. 5, 2006 (EP) ..................... 06450176

(51) Int. Cl.
*A61K 36/82* (2006.01)
(52) U.S. Cl. ........................................ 424/729
(58) Field of Classification Search .......... None
See application file for complete search history.

(56) References Cited

U.S. PATENT DOCUMENTS

| 5,002,934 | A | * | 3/1991 | Norton et al. | 514/54 |
|---|---|---|---|---|---|
| 5,556,703 | A | * | 9/1996 | Gross | 428/402 |
| 6,096,862 | A | | 8/2000 | Greve et al. | |
| 6,326,004 | B1 | | 12/2001 | Greve et al. | |
| 6,391,452 | B1 | | 5/2002 | Antonsen et al. | |
| 2003/0181415 | A1 | | 9/2003 | Zaneveld et al. | |
| 2003/0217416 | A1 | | 11/2003 | Litke et al. | |
| 2005/0171053 | A1 | | 8/2005 | Blakemore et al. | |
| 2008/0241271 | A1 | * | 10/2008 | Roman et al. | 424/641 |

FOREIGN PATENT DOCUMENTS

| DE | 198 25 395 C1 | 9/1999 |
|---|---|---|
| DE | 20 2005 014 019 U1 | 12/2005 |
| DE | 202005014019 U1 * | 12/2005 |
| EP | 0 523 803 A1 | 1/1993 |
| WO | WO 2005/004882 A1 | 1/2005 |
| WO | WO 2006/003521 A1 | 1/2006 |
| WO | WO 2007/102182 A1 | 9/2007 |

OTHER PUBLICATIONS

Gonzalez et al., "Polysaccharides as Antiviral Agents: Antiviral Activity of Carrageenan," *Antimicrobial Agents and Chemotherapy*, vol. 31, No. 9, Sep. 1987, pp. 1388-1393.

Yamada et al., "Preparation and anti-HIV activity of low-molecular-weight carrageenans and their sulfated derivatives," *Carbohydrate Polymers*, vol. 32, 1997, pp. 51-55.

De S. F-Tischer et al., "Chemical structure and antiviral activity of carrageenans from *Meristiella gelidium* against herpes simplex and dengue virus," *Carbohydrate Polymers*, vol. 63, 2006, pp. 459-465.

Carlucci et al., "Protective effect of a natural carrageenan on genital herpes simplex virus infection in mice," *Antiviral Research*, vol. 64, 2004, pp. 137-141.

Pujol et al., "Antiviral Activity of a Carrageenan from *Gigartina skottsbergii* against Intraperitoneal Murine Herpes simplex Virus Infection," *Planta Medica*, vol. 72, 2006, pp. 121-125.

* cited by examiner

*Primary Examiner* — Christophr R. Tate
*Assistant Examiner* — Deborah A. Davis
(74) *Attorney, Agent, or Firm* — Oliff & Berridge, PLC (57) ABSTRACT

A method for manufacturing an antiviral pharmaceutical composition for the prophylaxis or treatment of a rhinovirus infection that includes the utilization of iota-, kappa- or lambda-carrageenan or mixtures thereof.

19 Claims, 6 Drawing Sheets

ANTIVIRAL COMPOSITION AND METHOD OF USE

TECHNICAL FIELD

The present invention is in the field of immunology and antiviral agents and relates to a pharmaceutical composition comprising carrageenan as an active antiviral ingredient and to applications thereof in the prevention or therapeutic treatment of rhinovirus infections.

BACKGROUND OF THE INVENTION

Picornaviruses represent a very large virus family of small ribonucleic acid-containing viruses responsible for many serious human and animal diseases. Picornaviruses include four major groups: enteroviruses, rhinoviruses, cardioviruses and apthoviruses.

The human rhinoviruses consist of at least 100 serotypes and are the primary causative agents of the common cold. Because of the large number of serotypes, development of a vaccine is problematic; antiviral agents may therefore be the best approach to treatment. Rhinoviruses are composed of a surrounding capsid, which contains four viral proteins VP1, VP2, VP3 and VP4. Proteins VP1, VP2 and VP3 are organized into 60 repeating protameric icosahedral units. These are thought to be the cause of antigen diversity associated with these viruses.

Rhinovirus (HRV) infections lead to the common cold with symptoms such as fever, cough, and nasal congestion. HRV infection is the second most frequently recognized agent associated with pneumonia and bronchiolitis in infants and young children and commonly causes exacerbations of pre-existing airways disease in those with asthma, chronic obstructive pulmonary disease or cystic fibrosis. HRV infection is associated with one-third to one-half of asthma exacerbations depending on age and is linked to asthma hospitalizations in both adults and children.

Present treatment approaches include the application of rhinovirus specific RNA, as disclosed in the DE 19825395, which binds to the canyon region of the capsid, which is necessary to host receptor (e.g. ICAM-1, intercellular adhesion molecule-1) binding and cell infection.

Another method comprises the administration of soluble ICAM-1 proteins or derivatives of ICAM-1 as disclosed in the U.S. Pat. No. 6,326,004 and the U.S. Pat. No. 6,096,862 (tICAM-1, truncated ICAM-1) to neutralize viral particles (virions).

Chemical compounds with antiviral activity against rhinoviruses are disclosed in EP 0523803.

Rhinovirus symptoms are caused by an overly or unspecific reaction of the immune system. Therefore common treatment forms of a rhinovirus infection include administration of analgesics such as aspirin or acetaminophen/paracetamol, as well as localized versions targeting the throat (often delivered in lozenge form), nasal decongestants which reduce the inflammation in the nasal passages by constricting local blood vessels, cough suppressants (which work to suppress the cough reflex of the brain or by diluting the mucus in the lungs), and first-generation anti-histamines such as brompheniramine, chlorpheniramine, and clemastine (which reduce mucus gland secretion and thus combat blocked/runny noses but also may make the user drowsy).

Sulphated polysaccharides including carrageenans are known in the art for their antiviral efficacy. In a most interesting review, Gonzalez M. E. et al. (1987, Antimicrob. Agents Chemother. 31, 1388-1393) report an antiviral efficacy of different sulphated polysaccharides including iota-carrageenan against several animal viruses. Iota-carrageenan showed antiviral activity against the enveloped viruses HSV-1, HSV-2, Semliki Forest virus (SFV), vaccinia virus and African swine fever virus (ASF) and against the naked encephalomyocarditis (EMC) virus. Iota-carrageenan had no effect on the enveloped viruses vesicular stomatitis virus (VSV) and measles virus and on the naked viruses polio virus type 1 and adenovirus type 5.

US 2003/181415 A discloses antiviral activity of sulfated polysaccharides such as cellulose sulfate, against various enveloped viruses and in particular herpes simplex virus (HSV), Papilloma viruses and HIV.

WO 2005/004882 A discloses therapeutic treatment of viral infections, excluding rhinovirus infection, with sulphated polysaccharides such as carrageenans.

US 2005/171053 A1 discloses the use of lambda-carrageenan for inhibiting the spread of a sexually transmitted infection including HIV-1 infection.

Yamada et al. (1997, Carbohydrate Polymers, Appl. Scien. Publishers 32, 51-55) disclose an anti-HIV-1 activity of lambda-, kappa- and iota-carrageenan and their sulphated derivatives.

S. F. Tischer et al. (2006, Carbohydrate Polymers, Appl. Scien. Publishers 63, 459-465) disclose an activity of carrageenan isolated from *Meristiella gelidium* against herpes simplex and dengue virus.

Carlucci et al. (2004, Antiviral Research, Elsevier Science BV. 64, 137-141) disclose a protective effect of lambda-carrageenan on genital herpes simplex virus infection in mice.

Pujol et al. (2006, Planta Medica 72, 121-125) disclose an antiviral activity of a carrageenan isolated from *Gigartina skottsbergii* against intraperitoneal murine herpes simplex virus infection.

The term "carrageenan" is frequently used a collective term for linear sulphated galactose-based polysaccharides extracted from seaweed (rhodophyceae). It is mostly used as a thickener, gelling agent, stabilizer or emulsifier in pharmaceutical and food products. There exist more than 10 different carrageenans depending on the seaweed genus from which they are extracted. The three main types are iota-, kappa- and lambda-carrageenan, which differ slightly in their structure and degree of sulphatation. Iota-carrageenan is a soft-gel forming sulphated galactan predominantly extracted from red seaweed *Gigartina stellata* and *Chondrus crispus*. Kappa-carrageenan yields strong, rigid gels and is predominantly produced from *Kappaphycus cottonii*. Lambda-carrageenan, which is the most common form, is frequently used to thicken dairy products.

Despite the long known antiviral activity of some carrageenans against viruses such as, e.g. HIV or HSV, the mechanism of how carrageenans exhibit antiviral activity still needs clarification.

In the light of the above, the present invention now provides for a carrageenan-based antiviral composition suitable in the prophylactic or therapeutic treatment of rhinovirus infections (rhinitis).

Experiments leading to the present invention have surprisingly demonstrated that in spite of possible reservations in the art selected carrageenans exert antiviral activity against rhinovirus infections (rhinitis), with iota-carrageenan yielding the best results.

DESCRIPTION OF THE INVENTION

Therefore, the present invention in its first embodiment relates to the use of carrageenan as an active antiviral ingredient in the manufacture of a pharmaceutical composition for the prophylactic or therapeutic treatment of a rhinovirus infection.

The term "active antiviral ingredient" used herein refers to a carrageenan compound that when applied in an effective dose or amount interferes, directly or indirectly or both directly and indirectly, with the rhinovirus infection cycle of a eukaryotic cell, more specifically with at least one part of the rhinovirus infection cycle selected from the group consisting of virus penetration of a eukaryotic cell, virus replication in a eukaryotic cell, virus assembly, and virus release from the infected eukaryotic cell. It also encompasses any effect in unspecifically inhibiting a virus titer increase or in unspecifically reducing a virus titer level in a eukaryotic or mammalian host system. The term further refers to a compound that has prophylactic efficacy in that it protects from, at least to some extent, or reduces the likelihood of coming down with a viral infection.

The present pharmaceutical composition may thus be administered before or after the onset of a viral infection. The term "prophylaxis" or "prophylactic treatment" as used herein relates to the administration of the present pharmaceutical composition in order to protect from, at least to some extent, or reduce the risk of falling ill with a viral infection.

The term "therapy" or "therapeutic treatment" as used herein relates to the administration of the present pharmaceutical composition to a virus-infected individual in order to alleviate the pathological impact of the infection, including reduction in severity and/or frequency of emerging symptoms, or elimination of such symptoms, remediation of possible injuries caused by or associated with such viral infection, and including inhibition or prevention of secondary viral, bacterial, fungal or any other kind of microbial infection.

The collective term "carrageenan" as used hereinafter refers to a mixture of at least two of iota- kappa- and lambda-carrageenan homo- or heteropolymers, i.e. to a mixture of iota- and Lambda-carrageenan, a mixture of iota- and kappa-carrageenan, a mixture of kappa- and lambda-carrageenan, or a mixture of iota-, kappa- and Lambda-carrageenan homo- or heteropolymers, unless explicitly stated otherwise or unless a different meaning is derivable from the spirit of the pertinent disclosure.

A carrageenan homopolymer is a molecularly pure carrageenan compound of one type of either iota-, kappa- or Lambda-carrageenan. A carrageenan heteropolymer comprises subunits of at least two different kinds of carrageenans, preferably selected from the group consisting of iota-, kappa- and lambda-carrageenan subunits.

Where referred to hereinafter, the term "mixture" of carrageenans may also refer to a composition of matter comprising as an active antiviral ingredient at least one kind of carrageenan heteropolymer, the "mixture" thus primarily being a mixture of different carrageenan subunits as part of said at least one heteropolymeric carrageenan present in the composition.

In a further embodiment the invention relates to such an anti-rhinoviral composition for prophylactic or therapeutic use, wherein said rhinovirus infection is an acute or a chronic rhinovirus infection.

The present carrageenan-based composition is suitable for topical application to treat skin or mucosal inflammation. But also systemic, e.g. parenteral or oral application is possible, especially when adapted to contain primarily low molecular weight carrageenan fractions. The carrageenan useful in the present invention has a mean molecular weight ranging from about 15000 to 5000000 Da. The low molecular weight fraction comprises carrageenan at an average molecular weight ranging from about 15 000 to about 50 000 Da, the middle molecular weight fraction from about 50 000 to about 500 000 Da, and the high molecular weight fraction from about 500 000 to about 5 000 000 Da.

In a preferred embodiment the pharmaceutical composition is adapted for topical or mucosal use. Suitable galenic forms of the ready-for-use preparations are creames, gets, ointments, powders (including powders for inhalation), sprays, foams, or Liquid solutions such as skin lotions, gargle solutions or nose drops. Other suitable forms of galenic preparation will be evident to those of ordinary skill in the art, including, for example, the nasal drug delivery systems disclosed in U.S. Pat. No. 6,391,452.

Apart from the active antiviral ingredients the present composition typically comprises at least one pharmaceutically acceptable carrier, and optionally further additives or ingredients.

A suitable carrier may be a diluent, e.g. water or saline, an excipient, or another vehicle suitable and useful for the administration of the active ingredients. Optional additives may be selected from the group consisting of $SiO_2$, $TiO_2$, a binder such as microcrystalline cellulose, polyvinylpyrrolidone, gum tragacanth, gelatine, starch, lactose, lactose monohydrate, alginic acid or maize; a lubricant or surfactant such as magnesium stearate or sodium lauryl sulphate; a glidant, such as colloidal silicon dioxide; a sweetening agent such as sucrose or saccharin. Further additives in the preparation can be but are not limited to buffers or pH adjusting agents, e.g. selected from citric acid, acetic acid, fumaric acid, hydrochloric acid, malic acid, nitric acid, phosphoric acid, propionic acid, sulfuric acid, tartaric acid, or combinations thereof.

Further ingredients may be present, including non-carrageenan drugs or pharmaceutically active substances.

Carrageenan may be used in the form of any pharmaceutically acceptable salt, for example sodium salts of carrageenan may be used. Other pharmaceutically acceptable salts include, among others, potassium, lithium and ammonium salts of carrageenan.

In another embodiment the invention the composition is for topical use and comprises carrageenan in an amount of between 0.01% and 20%, preferably between 0.1% and 10%, most preferably between 0.5% and 5% by weight (w/w) of the preparation.

Usually, the composition will be provided as a non-pyrogenous, sterile preparation. In case of a liquid preparation sterility may be achieved, for example, by filtration through a suitable membrane filter. Methods for the manufacture of sterile or aseptic pharmaceutical compositions are well known in the art and are not part of the present invention.

However, the pharmaceutical composition of the present invention may also be coated onto solid surfaces of hygiene or sanitary items, for example facial hygiene or sanitation articles that are typically used in the oral and/or nasal areas such as nasal tissues or papers, and handkerchiefs. More specifically, the pharmaceutical composition may be applied, e.g. sprayed—much like disinfectants—onto gloves, hygiene tissues or papers including nasal tissues, in order to exert a virucide effect at least to some extent, thus contributing to reducing an individual's repeated self-infection by contaminated fingertips and also to reduce viral spread among different individuals that are in close, e.g. hand-to-hand, contact with each other. Depending on the nature of the sanitary or hygiene item, the item may be covered, wet, or otherwise impregnated with the pharmaceutical composition.

Such carrageenan-treated items may also include but are not restricted to cotton swabs, dust masks or facial masks.

Even lipsticks maybe formulated to contain an antiviral effective amount of carrageenan. These hygiene or sanitation articles can be used prophylactically or along with therapeutical treatment against a viral infection and may assist in the prevention or reduction of a risk of infection.

Accordingly, in one embodiment the invention relates to such a use, wherein the antiviral composition is applied to the solid surface of a hygiene or sanitation article, particularly of a hygiene or sanitary glove, tissue or paper, especially a nasal tissue or paper, by either coating or impregnation.

The iota-, kappa- and lambda-carrageenans useful in the present invention are commercially available but may also be prepared by extraction from seaweed plants pursuant to extraction procedures known in the art.

In its preferred embodiment the invention relates to the use of at least one member selected from the group consisting of the homo- and heteropolymers of iota-, kappa-, and lambda-carrageenan.

In a specific embodiment the antiviral pharmaceutical composition of the present invention is substantially free of carrageenan forms other than iota-, kappa-, and lambda-carrageenan, —although trace amounts of such other carrageenans may be present. For various applications, iota-carrageenan may substantially be the only kind of carrageenan present in the composition.

In another embodiment the invention relates the use of carrageenan in the manufacture of an antiviral composition, wherein the composition comprises either iota-, kappa- or lambda-carrageenan, or a mixture of at least two of said carrageenans, in an amount of 80% or more, 90% or more, 95% or more, or even 99% or more of all carrageenans present in the composition. The percentages are given in percent by weight (% w/w) relative to the dry weight of the carrageenans referred to.

In another embodiment the invention relates to such a use, wherein the composition comprises not less than 50%, not less than 70%, not less than 80%, and preferably not less than 95% (w/w) by dry weight of iota-carrageenan, relative to the total dry weight of all carrageenans present in the composition.

The above carrageenan concentration values likewise apply to homo- and heteropolymeric carrageenans.

Carrageenan was found to be non-toxic upon oral or dermal administration, or upon inhalation, even when applied at extremely high doses and was therefore classified as "generally recognized as safe" (GRAS) by the Food and Drug Administration (FDA).

In another embodiment, the invention relates to the use of carrageenans in the manufacture of an antiviral composition, which further comprises at least one additional pharmaceutically active, antiviral compound, preferably cellulose sulfate.

In another embodiment, the present invention relates to the use of carrageenan, preferably iota-carrageenan, in the manufacture of a pharmaceutical composition for prophylactic or therapeutic treatment of a bodily condition selected from the group consisting of microbial infection, inflammatory disease, allergy, and impaired or suppressed immune system, wherein the carrageenan is present in combination with at least one other pharmaceutically active compound or drug. In such a composition the carrageenan may exert anti-rhinoviral adjuvant function. Said at least one other pharmaceutically active compound or drug may be selected from the group consisting of a steroid, e.g. cortisone, and an antihistamine.

In another embodiment the antiviral pharmaceutical preparation is for the treatment or prophylaxis in an individual that is especially susceptible to or is at an increased risk of a rhinovirus infection such as a high-risk patient selected from the group consisting of an asthma patient, a person with allergies, and a person having an inflammatory disease.

BRIEF DESCRIPTION OF THE DRAWINGS

FIG. 1 shows the results of a HRV induced cell death inhibition assay (XTT-assay).
Ordinate=OD measured at 492 nm; abscissa=different test samples; 1=uninfected cells; 2=untreated, infected cells; 3=infected cells treated with iota-carrageenan; 4=infected cells treated with kappa-carrageenan; 5=infected cells treated with lambda-carrageenan.

FIG. 2 shows the determination of peak titers of supernatants from infected Hela cells by $TCID_{50}$ assays.
Ordinate=$TCID_{50}$ titer; abscissa=concentration of iota-carrageenan in µg/ml; U=untreated cells; T (treatment) =cells were infected for one hour and the indicated concentration of iota-carrageenan was added one hour after treatment; P (prophylaxis)=the virus suspension was preincubated with the indicated concentration of iota-carrageenan for on hour before infection. Further processing was identical to T: cells were infected at a multiplicity of infection of 0.01. The peak titers were observed at day 3 for HRV-2 (FIG. 2A) and at day 4 for HRV-14 (FIG. 2B).

FIG. 3 shows the efficacy of iota-carrageenan on inhibition of rhinovirus replication on infected human nasal epithelial cells determined by $TCID_{50}$ assays.
Ordinate=$TCID_{50}$ titer in logs; abscissa=concentration of iota-carrageenan in µg/ml; MOCK=untreated control cells.

In order that the invention described herein may be more fully understood, the following examples are set forth. The examples are for illustrative purposes only and are not to be construed as limiting this invention in any respect. It is further understood that the present invention shall also comprise variations of the expressly disclosed embodiments to an extent as would be contemplated by a person of ordinary skill in the art.

Example 1

Effect of Different Types of Carrageenans Against Human Rhinovirus Type 2 (HRV-2) and Type 14 (HRV-14)

Figure 1A:
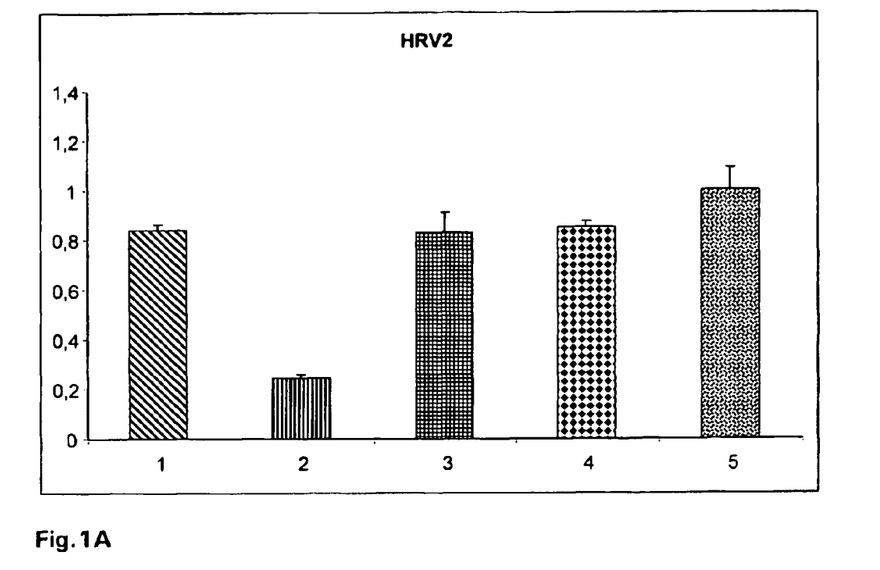
FIG. 1A=cells infected with HRV-2.
Figure 1B:
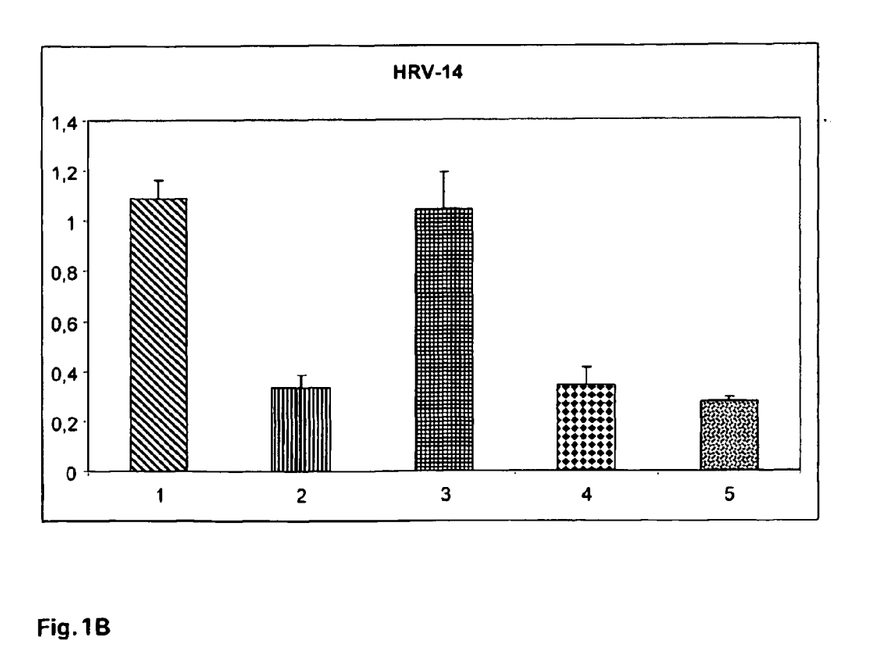
FIG. 1B=cells infected with HRV-14.
Figure 2A:
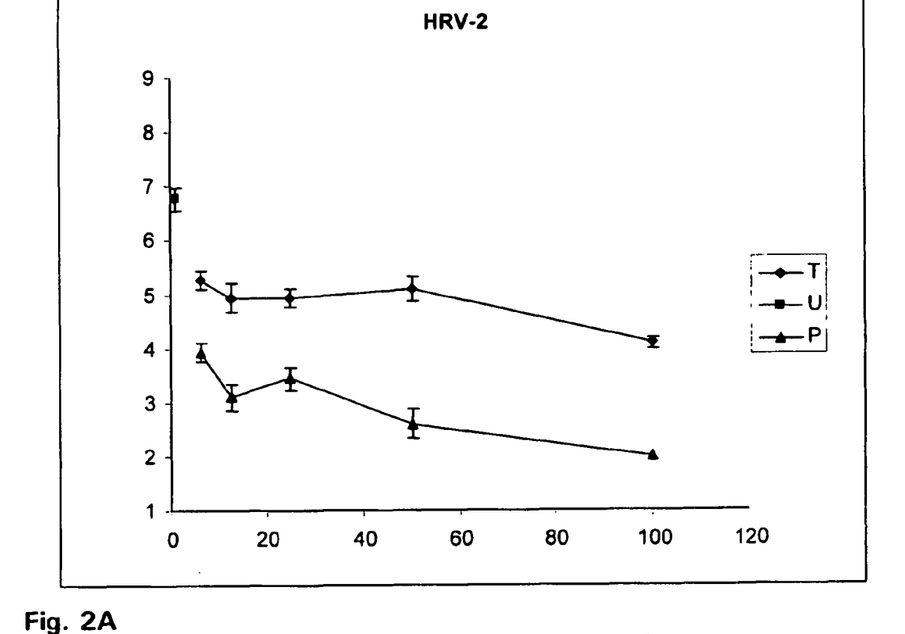
Figure 2B:
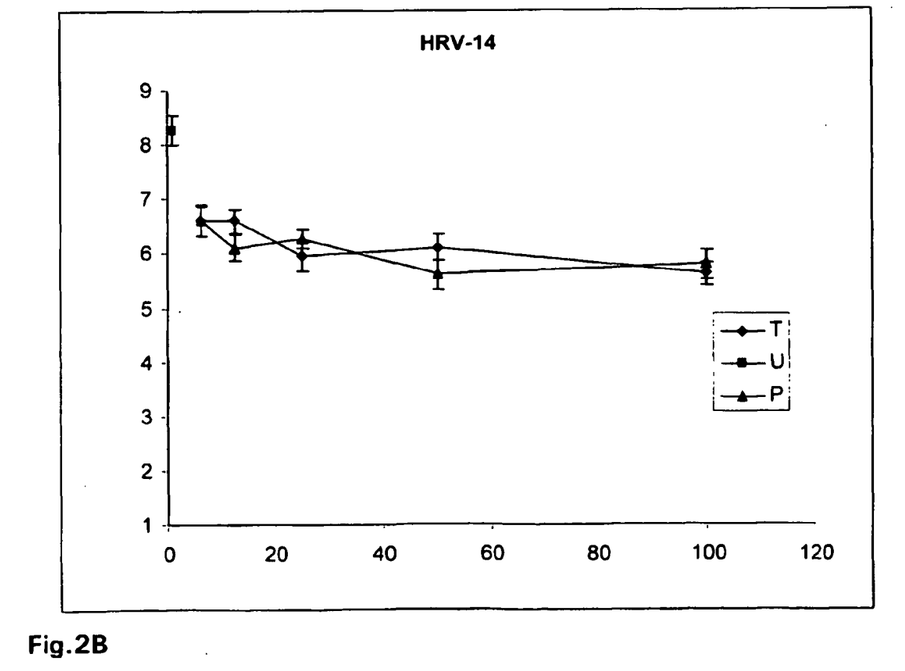
Figure 3A:
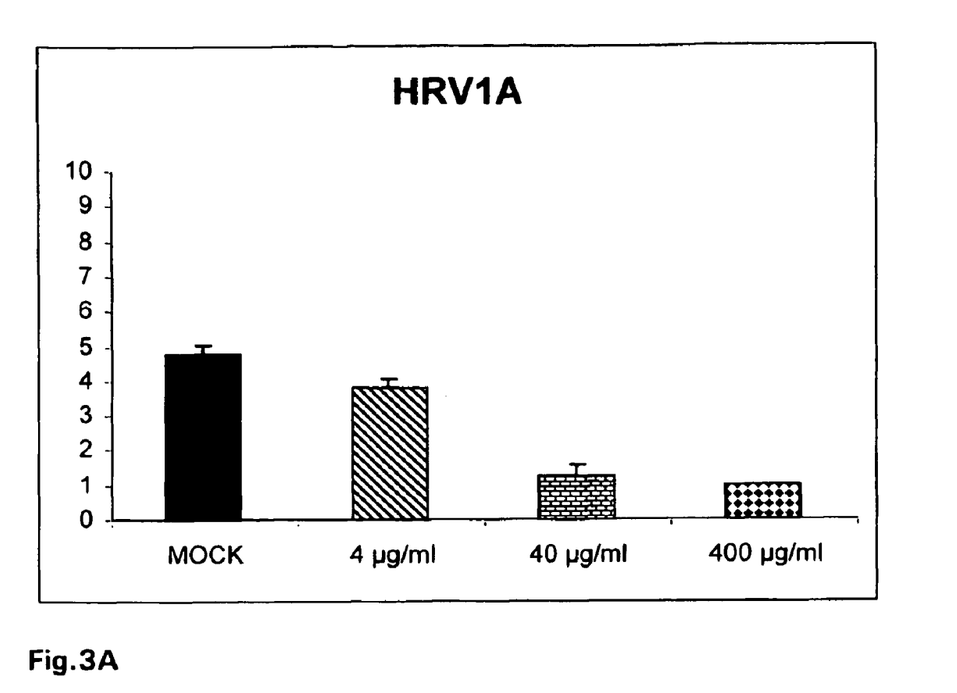
FIG. 3A=cells infected with HRV-1A.
Figure 3B:
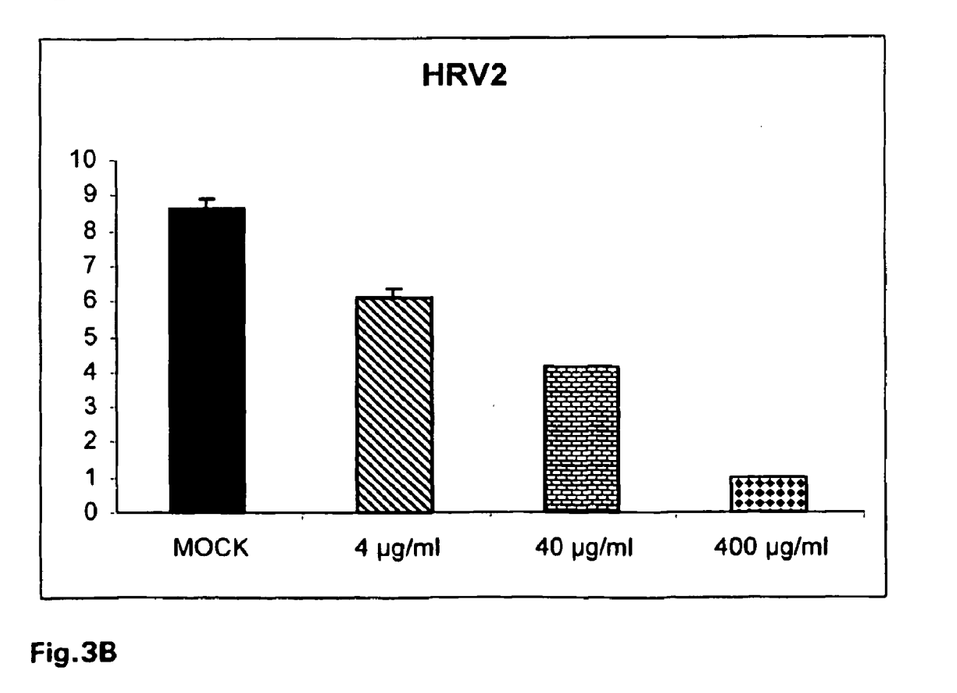
FIG. 3B=cells infected with HRV-2.
Figure 3C:
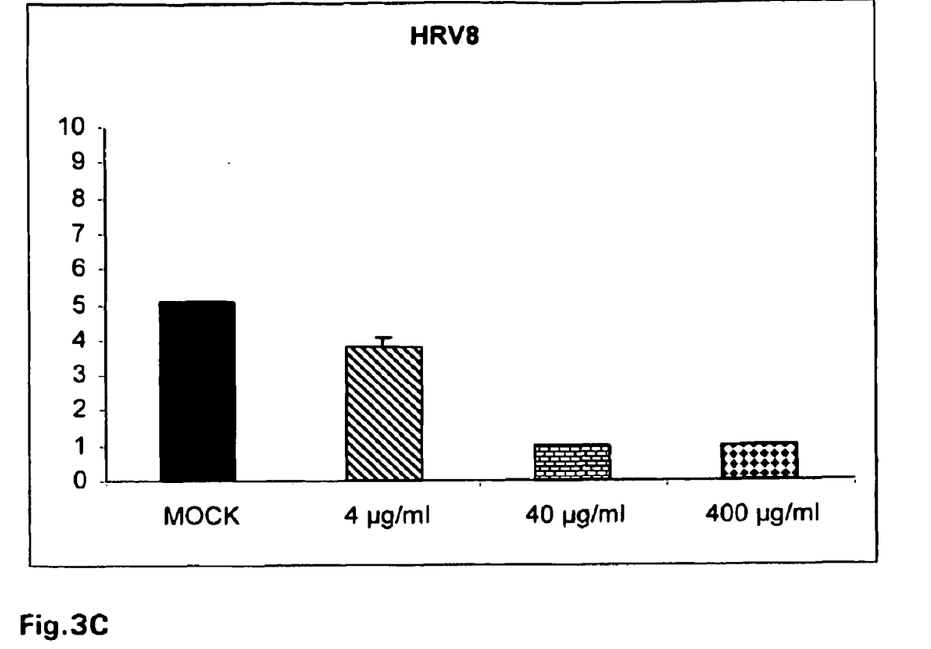
FIG. 3C=cells infected with HRV-8.
Figure 3D:
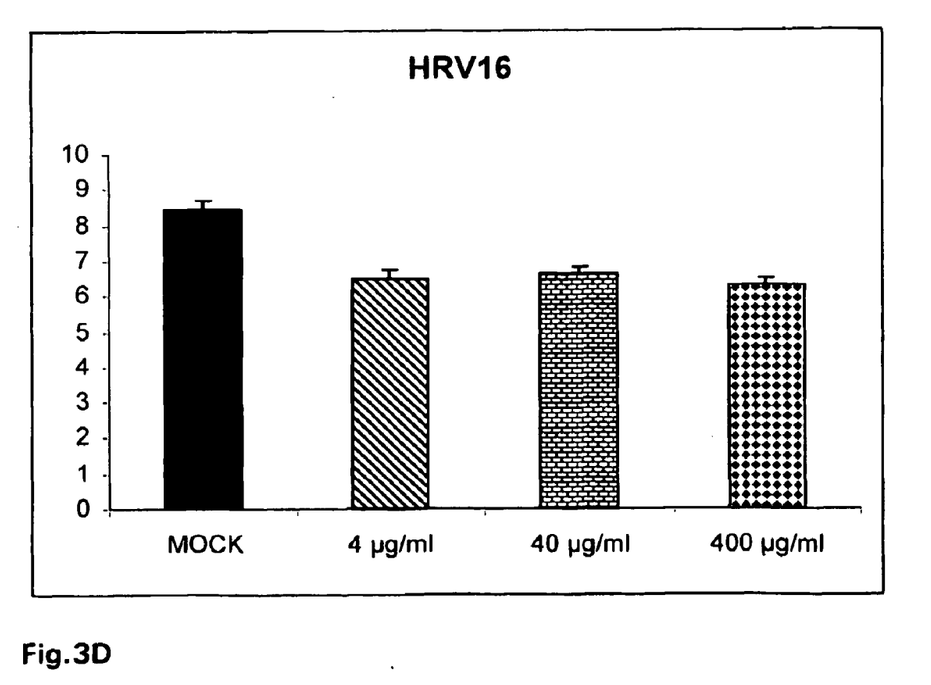
FIG. 3D=cells infected with HRV-16.
Figure 3E:
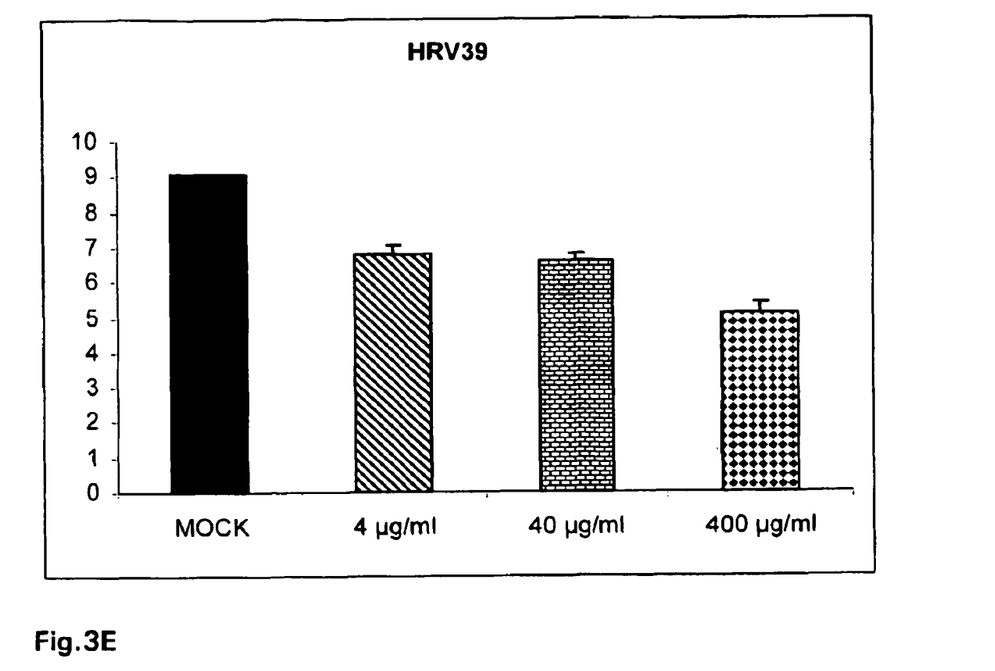
FIG. 3E=cells infected with HRV-39.
Figure 3F:
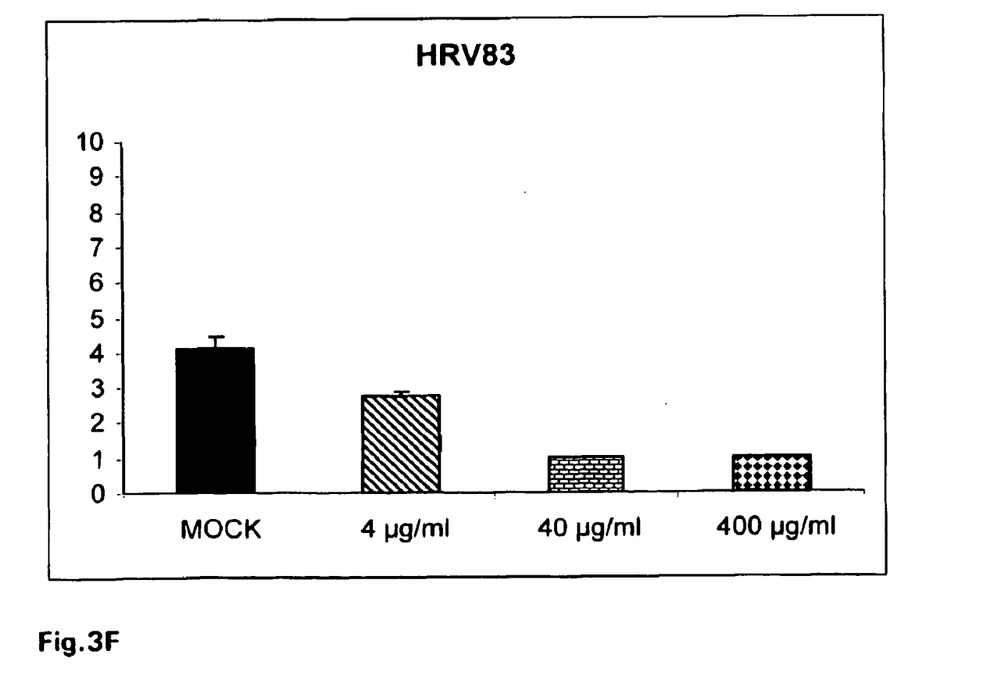
FIG. 3F=cells infected with HRV-83.

Subconfluent HeLa cells were incubated with a virus suspension that was preincubated for 5 min with 125 µg/ml of the polymers as indicated in FIG. 1. 48 hours later the viability of the cells was determined with TOX2 XTT assay (Sigma).

As shown in FIG. 1, it was found that the most effective polymer was iota-carrageenan (column 3) which was effective against both types of rhinovirus while, lambda-carrageenan (column 5) and kappa-carrageenan (column 4) showed efficacy against HRV-2 but not against HRV-14. Error bars indicate the standard deviation between six independent wells.

Example 2

The polymers indicated in Table 1 were tested in a HRV-2 and HRV-14 induced cell death inhibition assay (XTT-assay) at a concentration of 100 µg/ml.

As shown in Table 1, iota-carrageenan yielded protection against both types of rhinovirus (a "+" indicates at least 95% protection as compared with uninfected control cells). Kappa-carrageenan and lambda-carrageenan were active against HRV-2 but not against HRV-14. The polymers chitosan, carboxymethyl cellulose and carboxymethyl chitosan did not show an inhibitory effect at all.

TABLE 1

Antiviral activity of several tested polymers

| Polymer | HRV-2 | HRV-14 |
| --- | --- | --- |
| Iota-Carrageenan | + | + |
| Kappa-Carrageenan | + | − |
| Lambda-Carrageenan | + | − |
| Chitosan | − | − |
| Carboxymethylcellulose | − | − |
| Carboxymethylchitosan | − | − |

Example 3

Iota-carrageenan was effective against HRV-2 and HRV-14 in a treatment and a prophylaxis viral replication model. A significant reduction of peak viral titer was observed at concentrations equal and higher than 6.25 µg/ml. However, iota-carrageenan was most effective in the prophylaxis model against HRV-2 in which a reduction of more than 99.9% in the peak viral titer was observed.

Example 4

Effect of Iota-Carrageenan Against a Selection of Human Rhinovirus Subtypes

Subconfluent HeLa cells in 96 well plates were incubated with a virus suspension at a MOI (multiplicity of infection) of 0.5.

20 min after infection with the virus suspension, nutrient medium containing polymer in 3-fold dilutions was added. 48-72 hours later the viability of the cells was determined with TOX2 XTT assay (Sigma). $EC_{50}$ values were calculated with the software Excel-Fit.

TABLE 2

| Virus | HRV-1 | HRV-2 | HRV-8 | HRV-14 | HRV-16 | HRV-39 |
| --- | --- | --- | --- | --- | --- | --- |
| $EC_{50}$ | 0.7 µg/ml | 21 µg/ml | <0.5 µg/ml | 400 µg/ml | 381 µg/ml | 117 µg/ml |

Iota-carrageenan was active against all tested human rhinoviruses on previously infected HeLa cells. Carrageenan concentrations needed to inhibit 50% of the cytopathic effect vary within a wide range of <0.5 µg/ml for HRV-8 and 400 µg/ml for HRV-14. This result indicates that iota-carrageenan inhibits the replication of a broad spectrum of rhinovirus subtypes on infected HeLa cells.

Example 5

Inhibition of Rhinovirus Replication on Human Nasal Epithelial Cells by Iota-Carrageenan Primary human nasal epithelial cells (Promocell) were seeded in 24 well plates ($2.9*10^4$ cells per well) and cultivated for three days at 37° C., 5% $CO_2$ and 95% humidity. The cells were infected at a confluency of nearly 60% with rhinovirus strains HRV-1A, HRV-2, HRV-8, HRV-14, HRV-16, HRV-39, HRV-83 and HRV-84. Rhinoviruses HRV-1A, HRV-2, HRV-8, HRV-16, HRV-39 and HRV-83 performed a lytic replication on human nasal epithelial cells. HRV-14 and HRV-84 did not lyse the cells and were therefore not subjected to further testing. Viruses were preincubated with iota-carrageenan at concentrations of 4, 40 and 400 µg/ml and a MOCK control. The MOI was 0.34. Supernatants were harvested between 48 and 72 hours after infection and used for $TCID_{50}$ titer determination. As shown in FIG. 3, treatment with iota-carrageenan reduced the viral titer of all viruses in the supernatants at least two log steps at a concentration of 40 µg/ml (>99%) when compared to MOCK treated control cells (the Y-axis shows the virus titer in logs). These data clearly demonstrate that iota-carrageenan inhibits the virus replication on primary human epithelial cells. Since it appears that at present there is no animal model for human rhinovirus in vivo testing available, the human nasal epithelial cells used herein represent the most important in vitro model currently available. Error bars indicate the standard deviation between three independent tested samples.

Example 6

Determination of the Efficacy of Iota-Carrageenan Against Rhinovirus Infection after Repeated Treatment (Check for Possible Development of Viral Resistance)

The original virus HRV2P0 and the virus HRV2P10, obtained after 10 selective replication rounds on HeLa cells, were tested in a CPE (cytopathic effect) reduction assay. HeLa cells ($8*10^4$ cells per well) were seeded in six well plates. The cells were infected with a suitable nutrient medium supplemented with carrageenan polymer at final carrageenan concentrations of 1.6, 5.3, 17, 50, 150 and 450 µg/ml, and further containing virus at a MOI of 0.1. As controls, one well was MOCK infected with virus-free, carrageenan-supplemented nutrient medium, and another one well was infected with a MOCK treated virus suspension, i.e. a virus suspension containing nutrient medium but no carrageenan. After an incubation time of 20 minutes following infection, the plates were washed twice and control medium (virus-free, supplemented with carrageenan at the selected concentrations) was added to all wells except to the mock-treated negative control (i.e. pure, uninhibited infection). Samples were taken from each experimental well as soon as a clear cytopathic effect was visible in the unprotected, negative control well. For the subsequent selection round, virus-containing supernatant sampled from those carrageenan-treated wells exhibiting a clearly detectable CPE relative to the uninfected control was used for infection of Hela cells. Typically, CPE responses were detectable in the experimental samples at the two lowest carrageenan concentrations only, i.e. at 1.6 and 5.3 µg carrageenan per 1 ml.

The procedure was repeated 10 times and the resulting virus samples were compared in a CPE inhibition test with the original virus stock. Briefly, 48 hours after infection a TOX2 reagent (Sigma) was added, $OD_{450nm}$ values were determined and the CPE reduction in % of the uninfected control was determined.

Figure 4:
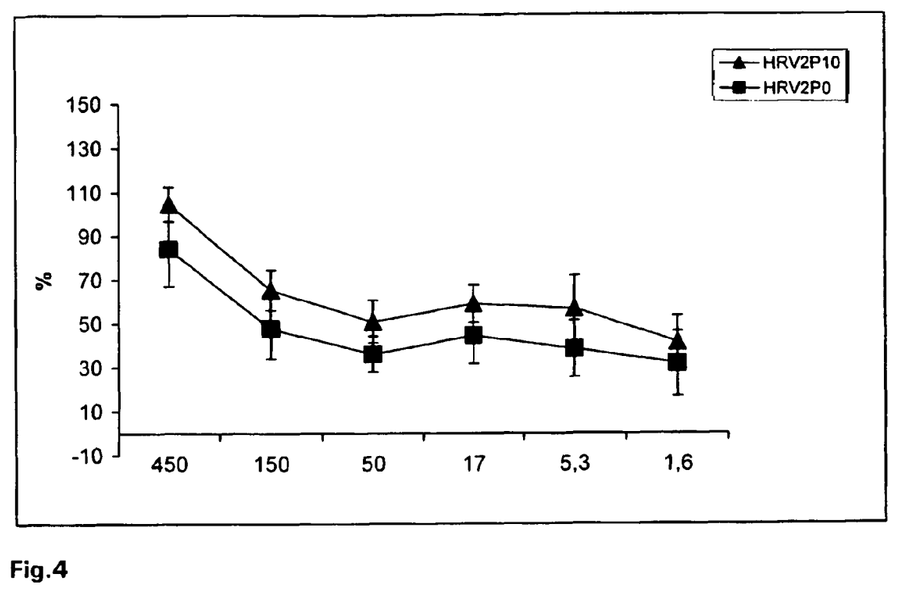
FIG. 4 shows the efficacy of iota-carrageenan against rhinovirus after repeated treatment determined by CPE reduction assay.
Ordinate=CPE reduction in %; abscissa=concentration of iota-carrageenan in µ/ml; Strain HRV2P0=original rhinovirus strain (no replication round); Strain HRV2P10=rhinovirus strain HRV2P0 after 10 selective replication rounds on HeLa cells.

In order to check for possible development of virus resistance towards carrageenan treatment, the virus used for the first inoculation (virus 2_001 in FIG. 4) and a virus obtained after 10 selective replication rounds (virus 20_001 in FIG. 4) were tested in a CPE reduction assay using HeLa cells, following an experimental protocol that was slightly different from the one described above. Briefly, HeLa cells were infected with the respective virus at a MOI of 0.1, and 20 minutes after infection the inoculum was removed and nutrient medium containing carrageenan polymer at final concentrations of 1.6, 5.3, 17, 50, 150 and 450 µg/ml was added (see abscissa of FIG. 4). 48 hours after infection a TOX2 reagent (Sigma) was added, OD450 nm values were determined and the CPE reduction in % of uninfected control was determined (FIG. 4, ordinate). Error bars indicate the standard deviation between 6 independent wells.

As graphically represented in FIG. 4, no significant difference in virus susceptibility towards carrageenan treatment was detected in the samples obtained from the supernatant of the first and the tenth infection cycle. This indicates that no escape mutants emerged during the selection procedure. These data thus suggest that an escape of rhinoviruses during in vivo therapy with iota-carrageenan may be unlikely even in cases of continued or repeated therapy over an extended period of time.

The invention claimed is:

1. A method for treating a subject having of a rhinovirus infection comprising administering to the subject a composition comprising iota-carrageenan in an antiviral effective amount as an active antiviral ingredient.

2. The method according to claim 1, wherein said rhinovirus infection is an acute or a chronic rhinovirus infection.

3. The method according to claim 1, wherein the composition is administered topically or mucosally.

4. The method according to claim 1, wherein the composition further comprises at least one pharmaceutically acceptable carrier or additive.

5. The method according to claim 1, wherein the composition is adapted for topical use and comprises iota-carrageenan in an amount of between 0.01% and 20% (w/v) of the composition.

6. The method according to claim 1, wherein the composition further comprises at least one other carrageenan, optionally selected from kappa-carrageenan and lambda-carrageenan.

7. The method according to claim 1, wherein the composition comprises not less than 50% (w/w), based on weight, of iota-carrageenan relative to a total of all carrageenans present in the composition.

8. The method according to claim 1, wherein the composition further comprises at least one other pharmaceutically active, antiviral component.

9. The method according to claim 1, wherein prior to the administering, the composition is coated onto a solid surface of a hygiene or sanitation article, and the administering comprises the subject contacting the coated surface of the hygiene or sanitation article.

10. The method according to claim 1, wherein the composition further comprises at least one other pharmaceutically active compound.

11. The method according to claim 1, wherein the subject is an individual being a high-risk patient selected from the group consisting of an asthma patient, a person suffering from allergy, and a person suffering from an inflammatory disease.

12. The method according to claim 3, wherein the composition is administered as a nose spray, a powder, including a powder for inhalation, a gel, an ointment, a foam, or a liquid solution including a lotion, a gargle solution, or drops.

13. The method according to claim 5, wherein the composition comprises iota-carrageenan in an amount of between 0.1% and 10% (w/v) of the composition.

14. The method according to claim 5, wherein the composition comprises iota-carrageenan in an amount of between 0.5% and 5% (w/v) of the composition.

15. The method according to claim 7, wherein the composition comprises not less than 80% (w/w), based on weight, of iota-carrageenan relative to a total of all carrageenans present in the composition.

16. The method according to claim 7, wherein the composition comprises not less than 95% (w/w), based on weight, of iota-carrageenan relative to a total of all carrageenans present in the composition.

17. The method according to claim 9, wherein the composition is coated onto a solid surface of a hygiene or sanitary glove, tissue or paper.

18. The method according to claim 9, wherein the composition is coated onto a solid surface of a nasal tissue or paper.

19. The method according to claim 10, wherein said at least one other pharmaceutically active compound is a steroid or an antihistamine.

* * * * *